US005635215A

United States Patent [19]
Boschetti et al.

[11] Patent Number: 5,635,215
[45] Date of Patent: Jun. 3, 1997

[54] MICROSPHERES USEFUL FOR THERAPEUTIC VASCULAR OCCLUSIONS AND INJECTABLE SOLUTIONS CONTAINING THE SAME

[75] Inventors: Egisto Boschetti, Croissy-sur-Seine; Michel Brouard, Belloy-en-France; Ludovic Drouet, Bourg-la-Reine; Pierre Girot, Paris; Alexandre Laurent, Courbevoie; Michel Wassef, Paris, all of France

[73] Assignees: BioSepra S.A., Villeneuve-La-Garenne Cedex; Assistance Publique Hôpitaux de Paris, Paris, both of France

[21] Appl. No.: 150,148

[22] PCT Filed: May 20, 1992

[86] PCT No.: PCT/US92/04265

§ 371 Date: Mar. 29, 1994

§ 102(e) Date: Mar. 29, 1994

[87] PCT Pub. No.: WO92/21327

PCT Pub. Date: Dec. 10, 1992

[30] Foreign Application Priority Data

May 29, 1991 [FR] France .................................. 91 06441

[51] Int. Cl.$^6$ ................. A61K 9/14; A61K 9/16; A61K 9/50
[52] U.S. Cl. .................... 424/501; 424/489; 424/491; 424/492; 424/496; 424/497; 424/500
[58] Field of Search ..................... 424/489, 491, 424/492, 496, 497, 500, 501

[56] References Cited

U.S. PATENT DOCUMENTS

| | | | |
|---|---|---|---|
| 4,413,070 | 11/1983 | Rembaum | 523/223 |
| 4,622,362 | 11/1986 | Rembaum | 525/54.1 |

OTHER PUBLICATIONS

Boschetti, E., "Polyacrylamide derivatives to the service of bioseparations," *Journal of Biochemical and Biophysical Methods* 19: 21–36 (1989).

Laurent et al., "Etude Histologique de Plusieurs Materiaux D'Embolisation et d'un Nouveau Type de Material Spherique et Adhesif," *Innovation et Technologie en Biologie et Medecine* 10(3): 357–366 (1989).

Mazza et al., "Polymer Design in Dye Chromatography: From the definition of monomers to the evaluation of polymeric supports," in *Protein–Dye Interactions: Developments and Applications*, Vijayalaksnmi M.A. ed., Elsevier Appl. Sciences, Elsevier Sci. Publ. Ltd., pp. 126–136 (1989).

Brown et al., "Syntheses and copolymerizations of new water–soluble polyiodinated acrylic monomers," *Makromol. Chem., Rapid Commun.* 6: 503–507 (1985).

Obrenovitch et al., "Microcarrier culture of Fibroblastic Cells on Modified Trisacryl Beads," *Biol. Cell* 46: 249–256 (1982).

*Primary Examiner*—Carlos Azpuru
*Attorney, Agent, or Firm*—Pennie & Edmonds

[57] ABSTRACT

The present invention concerns the use of microspheres for therapeutic embolization consisting of a hydrophilic acrylic copolymer coated with a cell adhesion promoter.

12 Claims, No Drawings

MICROSPHERES USEFUL FOR THERAPEUTIC VASCULAR OCCLUSIONS AND INJECTABLE SOLUTIONS CONTAINING THE SAME

This invention concerns the subject of materials for embolization. In particular, it concerns new calibrated and adhesive particles, especially suited to embolization.

Therapeutic vascular occlusions (embolizations) are techniques used to treat certain pathological conditions in situ. They are practiced generally by means of catheters making it possible, under imagery control, to position particulate occlusion agents (emboli) in the circulatory system. They can concern the vessels of various processes: tumors, vascular malformations, hemorrhagic processes, etc. Notably, in the case of tumors, vascular occlusion can suppress pain, limit blood loss on the surgical intervention to follow embolization or even bring on tumoral necrosis and avoid the operation. In the case of vascular malformations, it enables the blood flow to the "normal" tissues to be normalized, aids in surgery and limits the risk of hemorrhage. In hemorrhagic processes, vascular occlusion produces a reduction of flow, which promotes cicatrization of the arterial opening(s).

Furthermore, depending on the pathological conditions treated, embolization can be carried out for temporary as well as permanent objectives.

Different types of emboli are known in the prior art. In particular, liquid agents (acrylic glues, gels, viscous suspensions, etc.) or particulate agents (miscellaneous polymers, dura mater, gelatin sponges, spheres, balloons, spirals, etc.) can be involved. The major disadvantages of the known liquid emboli reside in their toxicity to the tissues, which can generate necrosis phenomena, and in the risk sticking of the catheters.

The disadvantages of the solid emboli available are essentially due to their nonspherical and hard-to-calibrate shape, to their nonhydrophilic character, to their hardness or even to their very high cost.

The present invention makes it possible to remedy the above-mentioned disadvantages. The applicant has, in fact, uncovered particularly advantageous properties of certain spherical materials, making possible their very effective use as emboli. The invention also resides in new emboli obtained by modifications of those materials, with a view to their application in embolization.

One object of the invention resides more specifically in the use of microspheres comprising an hydrophilic acrylic copolymer coated with a cell adhesion promoter.

In particular, the invention concerns the use of microspheres of diameter ranging between about 10 to about 2,000 µm.

Surprisingly, the microspheres defined above, present properties very advantageous for embolization. Notably, they are the only emboli combining properties of effectiveness, biocompatibility and stability.

More precisely, the microspheres used in the invention affords a 100% occlusion of the vascular lumen. Furthermore, they are easily calibrated, which makes possible a control of the distance of the occlusion. Finally, they are nonresorbable and nonbiodegradable, which allows for a durable occlusion.

On the other hand, these microspheres are nontoxic, biocompatible in vitro (with numerous cell lines) as well as in vivo and adhesive to the vascular wall through the cell growth they promote.

These microspheres are also stable. Thus, they are both flexible and deformable, in order to pass into small catheters without undergoing alteration, but perfectly resistant to the pressures generated by the embolization operations. They are likewise thermally stable, in order to be sterilized or frozen, and stable in suspension, in order to be preserved in suspension and injected with different liquids.

Finally, their hydrophilic character enables them to be placed in suspension, notably, in the form of sterile and pyrogenic injectable solutions, without formation of aggregates nor adhesion to the walls of the catheters, syringes, needles and other materials used in embolization.

The hydrophilic acrylic copolymer preferably comprises in copolymerized form about 25 to about 98% neutral hydrophilic acrylic monomar by weight, about 2 to about 50% difunctional monomer by weight and about 0 to about 50% by weight of one or more monomers carrying a cationic charge.

The presence of a cationic charge on the surface of the microsphere makes it possible to initiate and improve cell adhesion.

By way of example, the copolymers described in French Patent 2,378,808 can be suitable in this invention in formation of the base copolymer.

As hydrophilic acrylic monomer, the acrylamide and its derivatives, the methacrylamide and its derivatives or the hydromethylmethacrylate can be more specifically cited.

As example of difunctional monomer, the N,N'-methylene-bis-acrylamide, N'N'-diallyltartradiamide or even the glyoxal-bis-acrylamide can be cited.

Finally, as monomer having a cationic charge, those carrying a tertiary or quaternary amine function are preferred, such as diethylaminoethyl acrylamide, methacrylamidopropyl trimethylammonium or even acrylamidoethyl triethylammonium.

In a particularly advantageous manner, a copolymer comprising about 25 to about 98% methacrylamide by weight, about 2 to about 50% N,N-methylene-bis-acrylamide by weight, is used.

Different types of cell adhesion promoters cam be employed. In particular, the cell adhesion promoters can be of collagen, gelatin, glucosaminoglycans, fibronectins, lectins, polycations (polylysine) or any other natural or synthetic biological cell adhesion agent.

The cell adhesion promoter advantageously represents in the microsphere between about 1 and about 50% by volume of the hydrophilic acrylic copolymer.

In one particularly advantageous embodiment of the invention, it is possible to increase the stability of the microspheres in reticulating the adhesion agent. By way of example, in the case of gelatin, the reticulating agent can be chosen among the difunctional chemical agents reacting on the gelatin aminos (glutaraldehyde, formaldehyde, glyoxal, and the like).

Furthermore, the applicant has also developed new microspheres derived from those previously described, making possible a much easier application in embolization. Notably, one of the disadvantages of the materials described in the prior art is the difficulty the user has in visualizing them before, during and after injection under the naked eye or under imagery.

This problem is solved by a variant of the invention, consisting of identifiable microspheres containing an hydrophilic acrylic copolymer coated with a cell adhesion promoter and a marker. That property of microspheres can be obtained by modification during their synthesis or after their synthesis.

During their synthesis, the modifications can be obtained by incorporation with the other copolymer of a functionalized monomer carrying an identifiable function making detection of the microsphere possible.

For that purpose, a more particular object of the invention re-sides in microspheres for embolization comprising a copolymer comprising, in copolymerized form, about 25 to about 98% neutral hydrophilic acrylic monomer by weight, about 2 to about 50% difunctional monomer by weight, 0 to 50% by weight of one or more monomers carrying a cationic charge, and about 1 to about 30% by weight of a functionalized monomer making possible the detection of the microsphere, coated with a cell adhesion promoter.

More preferentially, microspheres having a diameter ranging between about 10 and about 2,000 μm are involved.

As neutral hydrophilic acrylic monomer, as difunctional monomer, as charged monomers and as cell adhesion agent, those previously defined can be used.

The functionalized monomer is generally obtained by chemical coupling of the monomer with a marker, which can be:

- a chemical dye, such as Cibacron Blue or Procion Red HE-3B, making possible a direct visualization of the microspheres [Boschetti, *J. Biochem-Biophys. Meth.* 19: 21–36 (1989)]. One can mention as functionalized monomer usable for this type of marking N-acryloyl hexamethylene Cibacron Blue or N-acryloyl hexamethylene Procion Red HE-3B,
- a magnetic resonance imaging agent (erbium, gadolinium, magnetite) or even
- a contrasting agent, such as barium or iodine salts. One can mention, by way of example, (acrylamino-e-propion-amido)-3-triiodo-2,4,6-benzoic acid, which can be prepared under the conditions described by Boschetti et al. (*Bull. Sec. Chim.* France, 1986 No. 4).

In the case of barium or magnetite salts, they can be directly introduced in powdered form in the initial monomer solution.

As indicated above, it is also possible to mark the microsphere after their synthesis. This can be done, for example, by grafting of fluorescent markers such as erythrosine or fluorescein or their derivatives (FITC, EITC, and the like).

Another object of the invention concerns injectable solutions containing microspheres, as previously defined. It preferably involves injectable solutions containing microspheres distributed in approximately 200 μ caliber segments.

The applicant has, in fact, shown that, by using restricted caliber segments, the efficacy of occlusion and its distal control were markedly improved. Such injectable solutions thus make it possible to improve the efficacy of occlusion and to adapt treatment to the diameter and nature of the vessel to be embolized and to the process involved.

The microspheres of the invention can be obtained by standard methods of polymerization described in the prior art (French Patent 2,378,808). In general, the polymerization of monomers in solution is carried out at a temperature ranging between about 0° C. and about 100° C. and between about 40° C. and about 60° C., in the presence of a polymerization reaction initiator.

The polymerization initiator is advantageously chosen among the redox systems, Notably, it is possible to use combinations of an alkali metal persulfate with N,N,N',N'-tetramethylethylenediamine or with dimethylaminopropionitrile, organic peroxides such as benzoyl peroxide or even 2,2'-azo-bis-isobutyronitrile.

The quantity of initiator used is adapted by one skilled in the art to the quantity of monomors and the rate of polymerization sought.

Polymerization can be carried out in mass or in emulsion.

In the case of a mass polymerization, the aqueous solution containing the different dissolved constituents and the initiator undergoes a polymerization in a homogeneous medium. It makes it possible to access a lump of aqueous gel which can then be separated into microspheres, by passing, for example, through the mesh of a screen.

Emulsion polymerization is the preferred method of preparation, since it makes it possible to access directly microspheres of a desired size. It can be conducted as follows: the aqueous solution containing the different dissolved constituents (different monomers, cell adhesion agent) is mixed, stirring, with a liquid organic phase not miscible in water, possibly in the presence of an emulsifier. The rate of stirring is adjusted so as to obtain an aqueous phase emulsion in the organic phase forming drops of desired diameter. Polymerization is then started off by addition of the initiator. It is accompanied by an exothermic reactions and its development can then be followed by measuring the temperature of the reaction medium.

It is possible to use as organic phase vegetable or mineral oils, certain petroleum distillation products, chlorinated hydrocarbons or a mixture of those different solutions. Furthermore, in case the polymerization initiator includes several components (redox system), it is possible to add one of them in the aqueous phase before emulsification.

The microspheres thus obtained can then be recovered by cooling, decanting and filtration. They are then separated by size category and washed to eliminate any trace of secondary product.

The polymerization stage can be followed by a stage of reticulation of the cell adhesion agent and possibly by a marking stage in the case of microspheres rendered identifiable by grafting after synthesis.

This invention will be more completely described by means of the following examples, which are to be considered illustrative and not limitative.

EXAMPLE 1

In a beaker containing 100 ml of demineralized water, 58 g of sodium chloride and 27 g of sodium acetate are dissolved. One adds 400 ml of glycerol and then the pH is adjusted between 5.9 and 6.1. Then 90 g of N-tris-hydroxymethyl methylacrylamide, 35 mg of diethylaminoethylacrylamide and 10 g of N,N-methylene-bis-acrylamide are added. One heats at 60°–70° C. and 100 mo of a hot 300 mg/ml gelatin solution is added. The total volume of the mixture is adjusted to 980 ml by addition of hot water and then 20 ml of a 70 mg/ml ammonium persulfate solution and 4 ml of N,N,N',N'-tetramethylethylenediamine are added.

This solution is poured into paraffin oil at 50°–70° C. stirring. After a few minutes, the polymerization reaction of acrylic monomers is manifested by an increase of temperature. The microspheres are then recovered by decanting, washed carefully, screened and sterilized in an autoclave in a buffered medium.

Those microspheres, after screen calibration, possess the characteristics desired for embolization, including a marked cationic charge and an effective adhesion agent (gelatin or denatured collagen).

EXAMPLE 2

The procedure of Example 1 is followed, using triethylaminoethyl acrylamide instead of diethylaminoethyl acrylamide.

After recovery of the spheres, the gelatin is reticulated by means of a 25% glutaraldehyde solution (100 ml of all of the microspheres). The treatment is carried out stirring at 4° C. overnight. It is followed by a washing with demineralized water.

EXAMPLES 3 AND 4

The procedure of Examples 1 and 2 is followed, replacing 10 g of N-tris-hydroxymethyl methylacrylamide with 10 g of N-acryloyl hexamethylene Cibacron Blue.

The microspheres obtained possess an intense blue coloration due to the integration of the acrylic dye in the polymer lattice.

Those microspheres are advantageously usable in direct view of the user at the time of handling.

EXAMPLES 5 and 6

The procedure of Examples 1 and 2 is followed, replacing N-tris-hydroxymethyl methylacrylamide with 10 g of N-acryloyl hexamethylene Procion Red HE-3B.

The microspheres obtained possess an intense red coloration due to the integration of the acrylic dye in the polymer lattice.

Those microspheres are advantageously usable in direct view of the user at the time of handling.

EXAMPLES 7 AND 8

One hundred milliliters of microspheres obtained according to Examples 1 and 2 are washed with a 0.1 M borate buffer of pH 8 and then suspended in 50 ml of a 5 mg/ml erythrosine isothiocyanate solution. The suspension is then stirred for at least 15 hours, after which it is washed with a neutral buffer to a colorless supernatant.

Those red-colored microspheres are then calibrated and sterilized, and can be used in percutaneous embolization.

EXAMPLES 9 AND 10

The procedure of Examples 1 and 2 is followed, replacing 10 g of N-tris-hydroxymethyl methylacrylamide with 10 g of a monomer opaque to X-rays, (acrylamido-3-propionamido)-3-triiodo-2,4,6-benzoic acid.

The microspheres obtained possess the property of absorbing X-rays and are therefore of particular interest in their in vivo follow-up after embolization.

EXAMPLES 11 TO 14

The procedure of Examples 1 and 3 is followed, adding to the Initial monomer solution 5 g of a radio-opaque soluble linear polymer, acrylamino-3-triiodo-2,4,6-benzoic polyacid (Examples 11 and 12) or (acrylamino-3-propionamido)-3-triiodo-2,4,6-benzoic polyacid (Examples 13 and 14).

Those polymers, having a molecular weight exceeding 100,000 daltons, are imprisoned in the polymer lattice and, without disturbing the general properties of the microspheres for the applications claimed, make it possible to attain a radiopacity usable for the in vivo follow-up of embolization operations.

EXAMPLES 15 AND 16

The procedure of Examples 1 and 2 is followed, adding to the initial monomer solution 200 g of barium sulfate power. The microspheres obtained are opaque to both visible light and X-rays.

EXAMPLES 17 AND 18

The procedure of Examples 1 and 2 is followed, adding 50 mg of magnetite ($Fe_3O_4$) to the initial monomer solution.

The microspheres obtained have the property of being detected in (Magnetic Resonance Imaging) MPI imagery.

EXAMPLE 19

Comparative Evaluation of Two Types of Nonresorbable Spheres

The study consisted of injecting two types of calibrated microspheres, some prepared according to Example 2, the others of polystyrene (Biosilin Nunc Danemark), in pulmonary arterial vascularization of the rat and of observing on days 0, 8 and 30 the extent of the cell reaction and the remodeling modalities of the occluded vessels.

The study revealed four important facts:

placement in suspension and vascular injection of the polystyrene spheres is difficult and clusters are formed at the segmental narrowing constituting the nozzle of the syringe, the base of the catheter and the possible changes of diameter of the catheters;

the cell reaction Is earlier, more intense and more durable with the spheres of Example 1 than with polystyrene. On the 8th day the thickness of the cell reaction covering the spheres of the invention is almost three times greater than that covering the polystyrene spheres (34 µ as compared to 13 µ);

there is no differences in kinetics th the vascular remodeling with either material;

no phenomenon suggesting the toxicity of either material was observed.

In conclusion, the microspheres of the invention are more manageable and more effective as adhesive agent.

EXAMLE 20

Clinical Evaluation in 89 Patients

One hundred procedures were carried out on various processes: 19 tumors, 75 arteriovenous malformations (12 facial AVM's, 40 medullary AVM's, 23 cerebral AVM's) and 6 miscellaneous (including hemorrhages).

The spheres used were spheres prepared according to Example 1, calibrated so as to obtain the following segments (in µm): 300–400, 400–600, 600–800, 800–1000 and 1000–1200, in suspension in ready-to-use bottles.

At the conclusion of this study, several remarks can be made:

1. The injection of these spheres is extremely simple and easier than with all of the other existing particles. At no time did any phenomenon like blocking of the systems necessary for injection (syringe, nozzle, base, connections, catheter, etc.) occur. Out of the 100 procedures, no accident occurred which might have been related to the equipment, its nature or shape. The follow-up of injection of the micropheres under radioscopy was easily secured by the addition of contrast products to the solution containing the microspheres in the injection syringe. No phenomenon of incompatibility between the microspheres and the different commercial vascular contrast products was observed.

2. In the case of tumors, devascularization could always be perfectly controlled with the two parameters of quantity of spheres and their diameter. Distribution of the spheres around fixed in narrow segments makes possible a better distal control of occlusion and command of the consequences of that occlusion: ischemia, necrosis, edema, etc. This is very important, particularly in conducting the embolization of certain tumors, like intracranial meningiomas, the tumoral necrosis of which can be accompanied by a severe edematous attack, compressing the healthy brain. The clinical course of 19 cases of tumors made it possible to uncover a new strategy of treatment of some of the tumors, consisting of embolizing in several stages with growing calibers in order to devascularize the tumor preoperatively.

3. In arteriovenous malformations the size required for the particles varied according to the process with, on first approach, the following tendencies:
facial AVM: 300, 500 μ
medullary AVM: 700, 900 μ
cerebral AVM: 900 to 1500 μ

4. Study of the correlation between angiographic devascularization and the histological data for two types of dispersion of microspheres in 16 embolized tumors, 8 with spheres distributed in broad segments (500±300 μ) and 8 in narrow segments (200±50 μ, 400±50 μ, 600±100 μ, 800±100 μ) revealed that the extent of necrosis and the number of intratumoral spheres are significantly greater in the group treated with spheres distributed over narrow segments than in the one treated with broad segments.

In conclusion: the microspheres of the invention are easy to use and effective for all processes and the tissue effects of occlusion are controllable when the size peaks are close together.

EXAMPLE 21

Comparative study of the durability of occlusion in medullary arteriovenous malformations treated with commercial nonspherical particles and microspheres prepared according to Example 1.

There were 84 afferent arteries of angiomas embolized: 48 with a nonspherical material and 26 with the microspheres.

The results of the study are:

total of almost total occlusion of the malformation by the microspheres was obtained in 25% of the cases, and an 80% closure was obtained in 50% of the cases. By comparison, 100% occlusion of the malformation was accomplished In only 5.4% of cases with nonspherical occlusion agents;

the course or the occlusion differs according to whether or not the occluding agent is spherical, since the rate of reopening in 9 months is 80% with nonspherical particles and 40% with the microspheres.

What is claimed is:

1. A microsphere, having a diameter ranging between about 10 to about 2000 μm, useful for embolization which comprises a hydrophilic acrylic copolymer coated with a cell adhesion promoter and a marking agent.

2. A microsphere having a diameter ranging between about 10 to about 2000 μm, useful for embolization, which comprises a copolymer comprising, in copolymerized form, about 25 to about 98% neutral hydrophilic acrylic monomer by weight, about 2 to about 50% difunctional monomer by weight, about 0 to about 50% by weight of one or more monomers having a cationic charge, and about 1 to about 30% by weight of a functional monomer making possible the detection of the microsphere, coated with a cell adhesion promoter.

3. A microsphere according to claim 2, characterized in that the functionalized monomer comprises a monomer covalently linked to a marking agent selected from the group consisting of dyes, imaging agents and contrasting agents.

4. A microsphere according to claim 3, characterized in that the functionalized monomer is selected from the group consisting of N-acryloyl hexamethylene-anthraquinone dyes, N-acryloyl hexamethylene-azoic dyes, (acrylamido-3-propionamido)-3-triiodo-2,4,6-benzoic acid or polymers thereof, polymerized form, and acryl-amido-3-triiodo-2,4,6, -benzoic polyacid.

5. A microsphere according to claim 3, characterized in that the marking agent is directly introduced in powdered form in the initial monomer solution.

6. The microsphere according to claim 1, characterized in that the acrylic copolymer comprises, in copolymerized form, about 25 to about 98% neutral hydrophilic acrylic monomer by weight, about 2 to about 50% difunctional monomer by weight, and about 0 to about 50% by weight of one or more monomers carrying a cationic charge.

7. The microsphere according to claim 6, characterized in that the neutral hydrophilic acrylic monomer is selected from the group consisting of acrylamides, methacrylamides and hydroxymethylmethacrylate.

8. The microsphere according to claim 6, characterized in that the difunctional monomer is selected from the group consisting of N,N'-methylene-bis-acrylamide, N'N'-diallyltartradiamide and glyoxal-bis-acrylamide.

9. The microsphere according to claim 6, characterized in that the monomer having a cationic charge is a monomer having a tertiary and/or quaternary amine function.

10. The microsphere according to claim 6, characterized in that the cell adhesion promoter is selected from the group consisting of collagen, gelatin, glucosaminoglycans, fibronectin, lectins, polycations, natural biological cell adhesion agents or synthetic biological cell adhesion agents.

11. The microsphere according to claim 10, characterized in that the cell adhesion promoter represents about 1 to about 50% by volume of the acrylic copolymer.

12. A microsphere having a diameter ranging between about 10 to about 2000 μm, useful for embolization, which comprises a copolymer comprising, in copolymerized form, about 25 to about 98% neutral hydrophilic acrylic monomer by weight, about 2 to about 50% difunctional monomer by weight, about 0 to about 50% by weight of one or more monomers having a cationic charge, a marking agent and a cell adhesion promoter.

* * * * *